(12) United States Patent
Satoh et al.

(10) Patent No.: US 7,291,113 B2
(45) Date of Patent: Nov. 6, 2007

(54) PULSE WAVE MEASURING APPARATUS THAT CAN CALCULATE EARLY SYSTOLIC COMPONENT AND LATE SYSTOLIC COMPONENT PROPERLY FROM ORIGINAL WAVEFORM

(75) Inventors: Hironori Satoh, Kyoto (JP); Tomoki Kitawaki, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 632 days.

(21) Appl. No.: 10/822,797

(22) Filed: Apr. 13, 2004

(65) Prior Publication Data

US 2004/0210145 A1  Oct. 21, 2004

(30) Foreign Application Priority Data

Apr. 16, 2003 (JP) ............................. 2003-111839

(51) Int. Cl.
*A61B 5/02* (2006.01)
(52) U.S. Cl. .................. 600/500; 600/485; 600/481
(58) Field of Classification Search ........ 600/485–507, 600/526
See application file for complete search history.

(56) References Cited

U.S. PATENT DOCUMENTS

| | | | |
|---|---|---|---|
| 4,858,616 A | | 8/1989 | Samaras et al. |
| 5,199,438 A | * | 4/1993 | Pearlman .................... 600/483 |
| 5,265,011 A | | 11/1993 | O'Rourke |
| 5,265,615 A | * | 11/1993 | Frank et al. ................. 600/485 |
| 6,017,313 A | * | 1/2000 | Bratteli et al. .............. 600/485 |
| 6,394,958 B1 | | 5/2002 | Bratteli et al. |
| 6,616,613 B1 | * | 9/2003 | Goodman .................... 600/504 |

FOREIGN PATENT DOCUMENTS

| | | |
|---|---|---|
| EP | 1 356 767 | 10/2003 |
| JP | 07-039530 | 2/1995 |
| JP | 2003010139 | 1/2003 |

OTHER PUBLICATIONS

European Search Report dated Aug. 30, 2004 relating to EP Application No. 04007707.5
Japanese Office Action dated Jan. 23, 2007, directed to counterpart JP application 2003-111839.

* cited by examiner

*Primary Examiner*—Charles A. Marmor, II
*Assistant Examiner*—Karen E Toth
(74) *Attorney, Agent, or Firm*—Morrison & Foerster LLP

(57) ABSTRACT

A pulse wave measuring apparatus obtains the N-th derivative of a measured pulse waveform. The pulse waveform is classified into waveforms α-δ in accordance with the presence/absence of a shoulder (inflection point) at a rising phase of a pulse waveform of one beat, and also in accordance with the presence/absence of a shoulder in a falling phase. In each classified waveform, each calculated characteristic point of the N-th derivative corresponds to a traveling wave or reflected wave. The pulse wave measuring apparatus can calculate an AI value or the like that is the characteristic value of a pulse wave using such characteristic points and calculation equation of each waveform.

16 Claims, 16 Drawing Sheets

| NUMBER OF 4DZC POINTS | | TYPE CLASSIFICATION | POSSIBILITY OF EXCESSIVE PRESSURIZATION |
|---|---|---|---|
| APG-A POINT ~ APG-B POINT | APG-B POINT ~ 1DZC POINT | | |
| 3 OR MORE POINTS | | ERROR | HIGH |
| 1 | 0~1 | $\gamma, \delta$ | MODERATE |
| 0 | 1 | $\gamma, \delta$ | LOW |
| 0 | 0 | $\alpha, \beta$ | NONE |

FIG.14

| TYPE | α | β | γ | δ |
|---|---|---|---|---|
| WAVEFORM | 1DZC ↓, APG-E ↓ | 1DZC ↓, 4IZC ↓↓ | 4DZC 4IZC ↓↓ | 1DZC ↓, 4DZC ↓ |
| TRAVELING WAVE | 1DZC | 1DZC | 4DZC | 4DZC |
| REFLECTED WAVE | APG-E | 4IZC | 4IZC | 1DZC |

(TYPE α)

(TYPE β)

(TYPE γ)

(TYPE δ)

ial waveform.

PULSE WAVE MEASURING APPARATUS THAT CAN CALCULATE EARLY SYSTOLIC COMPONENT AND LATE SYSTOLIC COMPONENT PROPERLY FROM ORIGINAL WAVEFORM

BACKGROUND OF THE INVENTION

1. Field of the Invention

The present invention relates to a pulse wave measuring apparatus, and a biological wave analysis program product. More particularly, the present invention relates to a pulse wave measuring apparatus and a biological wave analysis program product that can calculate the early systolic component and late systolic component properly from an original waveform.

2. Description of the Background Art

Blood pressure is the pressure exerted by the blood flow, generated by the contraction and expansion of the heart upon the inner wall of the artery. Systolic pressure that is the blood pressure corresponding to the systole of the heart and diastolic pressure that is the blood pressure corresponding to the diastole of the heart constitute blood pressure. The pulse pressure wave constituting the intra-arterial pressure is a superposed wave of the early systolic component (traveling wave) generated by ejection of blood from the heart and the late systolic component (reflected wave) generated by the reflection from mainly arterioles and capillary vessels. An inflection point is present between these two components.

The waveform of such a pulse wave changes as the measurement site becomes more distal. Specifically, the late systolic component becomes lower than the early systolic component in proportion to a more distal measurement site.

Japanese Patent Laying-Open No. 7-39530 discloses an automatic sphygmomanometer automatically analyzing the early systolic component and late systolic component by obtaining the wave of fourth derivative of the original waveform of a pulse wave.

Since the process of obtaining the late systolic component based on the original waveform and the wave of fourth derivative is employed, the conventional automatic sphygmomanometer disclosed in the aforementioned Japanese Patent Laying-Open No. 7-39530 has the problem that the late systolic component can not be obtained in the case where there are so many characteristic points of the wave of fourth derivative of the original waveform that the characteristic point is indefinite, or in the case where the method of obtaining the late systolic component used is a method directed to a measurement site differing from the relevant measurement site of the waveform. There is also the problem that the waveform of the pulse wave changes depending upon the generated timing and level of the reflected wave corresponding to the hardness of the vascular wall even if the pulse wave is measured at the same place.

SUMMARY OF THE INVENTION

In view of the foregoing, an object of the present invention is to provide a pulse wave measuring apparatus and a biological wave analysis program product that can classify a pulse waveform in advance, and calculate the early systolic component and late systolic component properly from the original waveform.

According to an aspect of the present invention, a pulse wave measuring apparatus includes a first calculation unit calculating a wave of multi-dimensional derivative from a pulse wave of one beat to obtain a characteristic point of multi-dimensional derivative, and a second calculation unit calculating, based on presence of a certain characteristic point of multi-dimensional derivative calculated by the first calculation unit in a predetermined interval of the pulse wave of one beat, one of the early systolic component and late systolic component corresponding to the predetermined interval, using the certain characteristic point of multi-dimensional derivative.

According to another aspect of the present invention, a biological wave analysis program product causes a computer to execute analysis of a biological wave that is a superposition of a first waveform and a second waveform. The biological wave analysis program product causes the computer to execute a first calculation step of calculating a wave of multi-dimensional derivative from a biological wave of one beat to obtain a characteristic point of multi-dimensional derivative, and a second calculation step of calculating, based on presence of a certain characteristic point of multi-dimensional derivative calculated by the first calculation step in a predetermined interval of the biological wave of one beat, one of the first waveform and the second waveform corresponding to the predetermined interval, using the certain characteristic point of multi-dimensional derivative.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 14 shows a scheme of classification of pulse waveforms.

DESCRIPTION OF THE PREFERRED EMBODIMENTS

Figure 1:
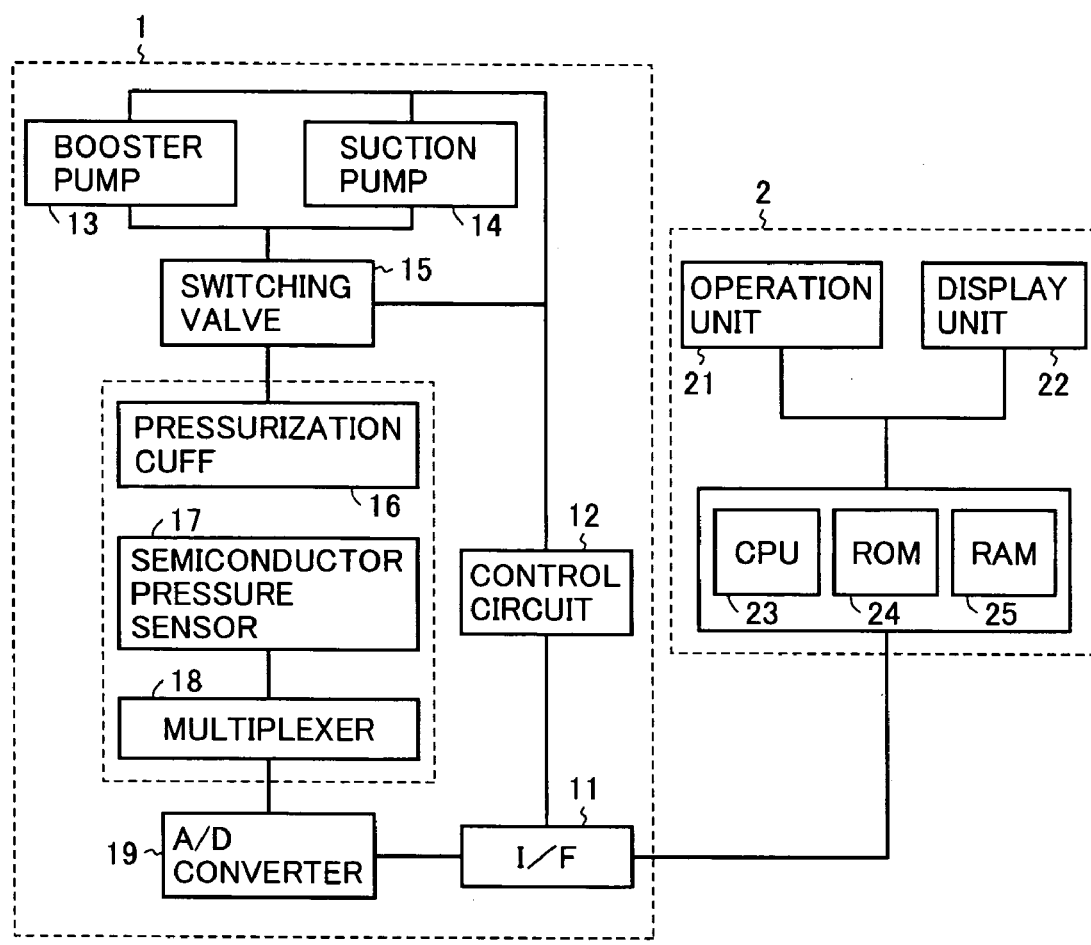
FIG. 1 shows a specific structure of a pulse wave measuring apparatus in accordance with an embodiment.

Embodiments of the present invention will be described hereinafter with reference to the drawings. In the following description, the same components and elements have the same reference character allotted. Their designation and function are identical. Therefore, detailed description thereof will not be repeated.

Referring to FIG. 1, a pulse wave measuring apparatus according to the present embodiment is mainly formed of a pulse wave device 1 detecting a pulse wave, and a control device 2 providing control of the entire pulse wave measuring apparatus. Pulse wave device 1 and control device 2 are connected through a dedicated cable such as a USB (Universal Serial Bus) cable, a communication line, or the like. It is assumed that connection thereof also includes non-contact connection such as radio communication.

Control device 2 includes a ROM (Read Only Memory) 24 and a RAM (Random Access Memory) 25 storing data and programs to control the pulse wave measuring apparatus, and a CPU (Central Processing Unit) 23 providing control of the entire pulse wave measuring apparatus. CPU 23 establishes access to ROM 24 to read out a program, which is transferred onto RAM 25 for execution, whereby overall control of the pulse wave measuring apparatus is effected. Control device 2 also includes an operation unit 21 operated to input various information provided in a manner operable from an external source, and a display unit 22 formed of a LED (Light Emitting Diode), a LCD (Liquid Crystal Display), or the like to output various information such as the artery position detection result and pulse wave measurement result. CPU 23 receives an operation signal through operation unit 21 designated by a user to carry out control processing of the pulse wave measuring apparatus based on the operation signal. Specifically, CPU 23 responds to the operation signal input through operation unit 21 to send out a control signal to pulse wave device 1. CPU 23 also displays the measurement result and the like received from pulse wave device 1 at display unit 22.

Control device 2 is generally a computer or the like. The structure of control device 2 shown in FIG. 1 is a specific example of a general computer structure. Therefore, the structure of control device 2 is not limited to that shown in FIG. 1.

Pulse wave device 1 receives the control signal from control device 2 via an I/F 11. The control signal received at I/F 11 is transmitted to a control circuit 12, and then to a booster pump 13, a suction pump 14, or a switching valve 15.

Booster pump 13 functions to increase the inner pressure (referred to as cuff pressure hereinafter) of a pressurization cuff (air bag) 16. Suction pump 14 functions to reduce the cuff pressure. Switching valve 15 selectively connects one of booster pump 13 and suction pump 14 to an air pipe (not shown). Control circuit 12 provides control thereof.

A semiconductor pressure sensor 17 includes a plurality of sensor elements aligned at a predetermined interval in one direction on a semiconductor chip formed of single crystalline silicon or the like. Semiconductor pressure sensor 17 is pressed against a measurement site such as the wrist of a subject during measurement by the pressure of pressurization cuff 16. Under this state, semiconductor pressure sensor 17 detects the pulse wave of a subject via an arteria radialis. Semiconductor pressure sensor 17 applies voltage signals output by detecting a pulse wave to a multiplexer 18 for each channel of respective sensor elements.

Multiplexer 18 selectively provides the voltage signal output from respective sensor elements to an A/D converter 19. A/D converter 19 converts the voltage signal that is an analog signal provided from semiconductor pressure sensor 17 into digital information. The digital information is transmitted to control device 2 via I/F 11. In the present embodiment, CPU 23 obtains at the same time voltage signals output from respective sensor elements in semiconductor pressure sensor 17 along the time axis via multiplexer 18.

In FIG. 1, the present sphygmograph apparatus is implemented with pulse wave device 1 and control device 2 to conduct pulse wave measurement in cooperation. Alternatively, the sphygmograph apparatus may include pulse wave device 1 and control device 2 in an integral manner.

The pulse wave measurement process carried at the pulse wave measuring apparatus of the present embodiment will be described here with reference to the flow chart of FIG. 2. The process of the flow chart of FIG. 2 is realized by CPU 23 of control device 2, establishing access to ROM 24 to read out a program therefrom, which is transferred onto RAM 25 for execution.

Figure 2:
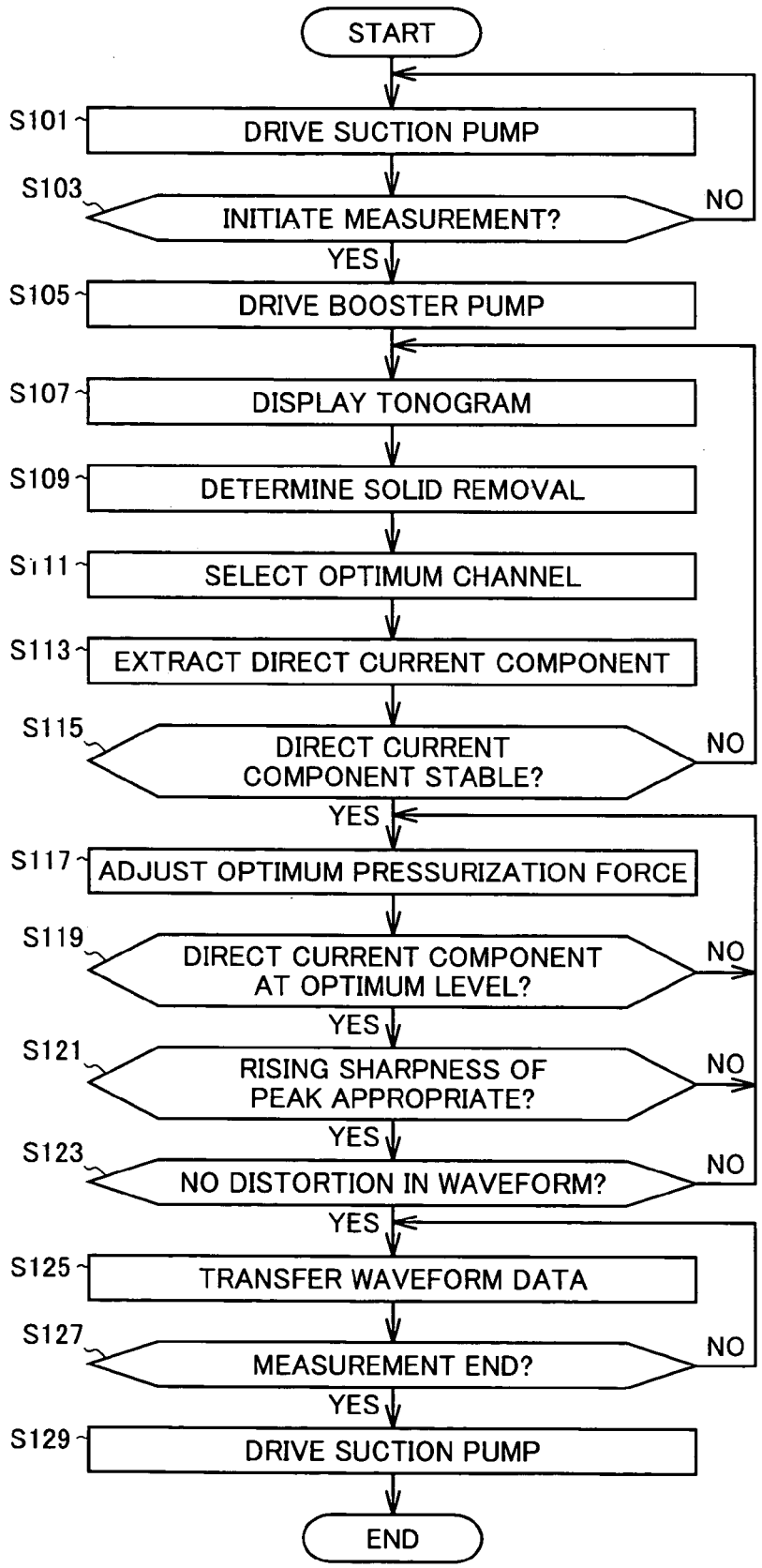
FIG. 2 is a flow chart of a pulse wave measurement process carried out at the pulse wave measuring apparatus of the embodiment.

Referring to FIG. 2, in response to a power switch (not shown) turned on, CPU 23 instructs control device 12 to drive suction pump 14 via I/F 11. In response to this instruction, control circuit 12 switches valve 15 towards suction pump 14 to drive suction pump 14 (S101). Suction pump 14 is driven so that the, cuff pressure is set sufficiently lower than the atmosphere through switching valve 15. This avoids unnecessary protrusion of the sensor unit including semiconductor pressure sensor 17 that will cause erroneous operation or failure.

Then, initiation of measurement is identified by detecting movement of the sensor portion to the measurement site, or depression of a measurement start switch (not shown) in operation unit 21 (S103). In the case of the former, the sensor portion includes a microswitch or the like not shown to sense movement CPU 23 determines whether the sensor portion has moved or not based on the detection signal of that micro switch.

When determination is made that measurement has initiated (YES at S103), CPU 23 sends a control signal to control device 12 via I/F 11 so as to drive booster pump 13. Control circuit 12 responds to this control signal to switch valve 15 towards booster pump 13 to drive booster pump 13 (S105). Accordingly, the cuff pressure rises, whereby the sensor unit including semiconductor pressure sensor 17 is pressed against the surface of the measurement site of the subject.

Upon pressurization of the sensor portion against the measurement site, voltage signals from respective sensor elements in semiconductor pressure sensor 17 are provided via multiplexer 18. The voltage signals are converted into digital information at A/D converter 19, and then applied to CPU 23 via I/F 11. CPU 23 generates a tonogram based on the received digital information. The generated tonogram is displayed at display unit 22 (S107).

CPU 23 determines the presence of solids such as the tendon, radius, or the like subcutaneous of the measurement site, based on the tonogram generated at step S107, to execute a process to remove the solid (S109). In this solid removal process, the sensor element with a sensing region in which the region above the solid is included is identified from the sensor elements in semiconductor pressure sensor 17, based on the information from the tonogram obtained at S107. The other sensor elements excluding the identified sensor element are selected as the candidates of sensor elements whose detection region corresponds to a region above an artery. The solid removal process is not limited to that described in the present invention. For example, the approach disclosed in Japanese Patent Application No. 2003-12313 previously filed by the applicant of the present invention can be used.

CPU 23 executes the process to select, from the candidates of sensor elements, the sensor elements whose detection region corresponds to a region above an artery as the optimum channels (S111). The process of selecting the optimum channels is not limited to that described in the present invention. The approach disclosed in the aforementioned Japanese Patent Application No. 2003-12313 can be employed.

CPU 23 extracts the direct current component from the voltage signals applied from respective sensor elements corresponding to the selected optimum channels (S113). The direct current component is obtained from the average value of voltage signals over a constant time, the component of the voltage signal passing through a low pass filter (component removed of pulse wave), or the level of the voltage signal at the pulse wave rising point (immediately before mixture of pulse wave component).

More particularly, the direct current component can be extracted at step S113 by dividing the output change of the voltage signal into windows (intervals) for each predetermined time, and calculating the average of each window. The direct current component can also be extracted by other ways such as calculating the intermediate value between the highest value and the lowest value in each window, or extracting a value below a predetermined frequency using a low pass filter. The aforementioned predetermined time is the time interval preset at the pulse wave measuring apparatus independent of the pulse beat of the subject. Preferably, the time interval is set to approximately 1.5 seconds in which the time of one pulse beat is included.

CPU 23 then detects the site where the direct current component extracted at step S113 from the voltage signals applied through respective sensor elements corresponding to the selected optimum channels is stable (S115). Upon detection of a site where the direct current component is stable (YES at S115), CPU 23 defines the pressurization force of pressurization cuff 16 at that time point as the optimum pressurization force, and sends a control signal to control circuit 12 via I/F 11 so as to adjust the pressure of pressurization cuff 16 (S117).

In the case where a site corresponding to a stable direct current component is not detected (NO at S115), the process of the above-described steps S107-S115 is repeated while continuing pressurization of pressurization cuff 16 through booster pump 13 until a site where the direct current component is stable is detected.

In addition, fine adjustment to maintain the pressurization force at the optimum level is conducted by repeating the determination process of steps S119-S123 set forth below even after a pressurization force of pressurization cuff 16 is defined as the optimum pressurization force at step S117: Specifically, CPU 23 continuously monitors whether the direct current component is stable or not under the state where the pressurization force of pressurization cuff 16 is adjusted at the optimum pressurization level (S119). For the purpose of maintaining the pressurization force of pressurization cuff 16 at the optimum pressurization level, adjustment of the pressurization force of step S117 is repeated, as necessary (NO at S119).

More specifically, at step S117, CPU 23 switches valve 15 to booster pump 13, and alters the pressurization force of semiconductor pressure sensor 17 by increasing the pressurization force of pressurization cuff 16 at a constant rate or an arbitrary rate through booster pump 13, or switches valve 15 to suction pump 14, and alters the pressurization force of semiconductor pressure sensor 17 by reducing the pressurization force of pressurization cuff 16 at a constant rate or arbitrary rate through suction pump 14 to adjust the pressurization force. The direct current component corresponding to the definition of the optimum pressurization force is compared with the direct current component succeeding adjustment of the pressurization force at step S119 so as to adjust, if necessary, the pressurization force, avoiding excessive pressurization.

Then, CPU 23 determines whether the rising sharpness of the peak of the voltage signal output from the sensor element selected as the optimum channel under the state where pressurization force of pressurization cuff 16 is maintained at the optimum pressurization level, i.e. the waveform data, is appropriate or not (S121), and further determines whether there is waveform distortion or not (S123).

When the rising sharpness of the peak of the waveform data is not appropriate (NO at S121), or when waveform distortion is detected (NO at S123), adjustment of the pressurization force of step S117 is repeated until the rising sharpness of the peak of waveform data becomes appropriate, or until waveform distortion is no longer detected.

When the rising sharpness of the peak of waveform data is appropriate (YES at S121), and when waveform distortion is not detected (YES at S123), CPU 23 acquires waveform data of that time point from pulse wave device 1 via multiplexer 18, A/D converter 19 and I/F 11 (S125).

CPU 23 detects a pulse wave from the waveform data acquired from pulse wave device 1 to determine establishment of a predetermined condition of waveform detection end (S127). The condition to end waveform detection of step S127 may be an elapse of a preset predetermined time, or an end (or interruption) instruction from a user. In other words, the above-described transfer process of pulse wave data of step S125 is repeated until a predetermined condition is established.

When the predetermined condition to end pulse wave detection is established (YES at S127), CPU 23 sends a control signal to control device 12 via I/F 11 so as to drive suction pump 14 via switching valve 15 (S129). Thus, the pressurized status of the sensor portion relative to the measurement site is released, and the series of pulse wave detection process ends.

A sensor signal analysis process carried out at the pulse wave measuring apparatus of the present embodiment will be described here with reference to the flow chart of FIG. 3. The process in accordance with the flow chart of FIG. 3 is realized by CPU 23 of control device 2, establishing access to ROM 24 to read out a program therefrom, which is transferred onto RAM 25 for execution.

Figure 3:
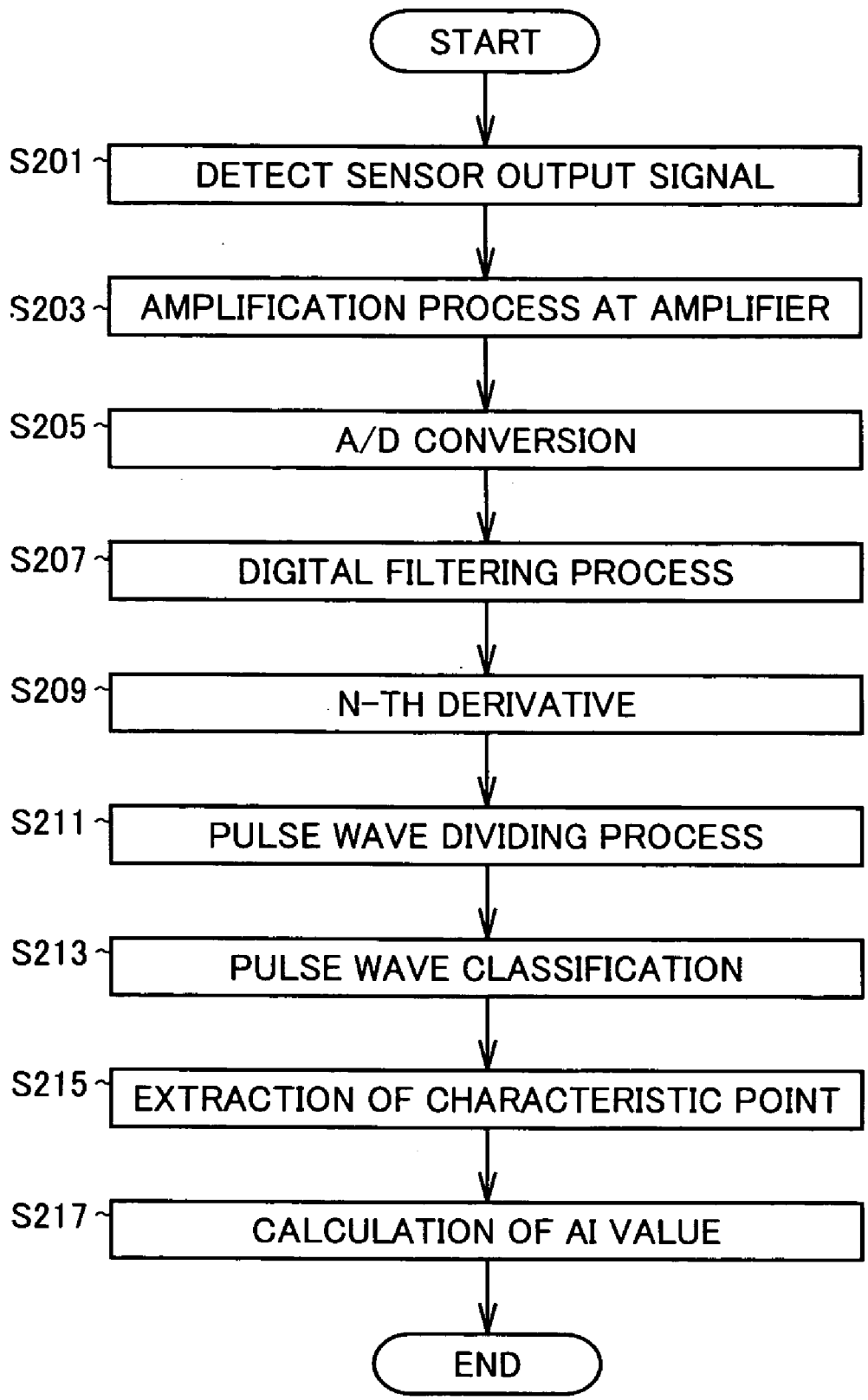
FIG. 3 is a flow chart of a sensor signal analysis process carried out at the pulse wave measuring apparatus of the embodiment.

Referring to FIG. 3, in response to detection of a pulse pressure sensor signal at semiconductor pressure sensor 17 (S201), semiconductor pressure sensor 17 provides a sensor signal to an amplifier not shown. The sensor signal detected at semiconductor pressure sensor 17 is amplified to a predetermined frequency by the amplifier (S203), and applied to A/D converter 19.

A/D converter 19 converts the sensor signal that is an analog signal from the amplifier into a digital signal (S205), and further applies a digital filtering process to extract the frequency of a predetermined range for the purpose of removing noise and the like (S207). Then, A/D converter 19 provides the digital sensor signal to control device 2 via I/F 11.

CPU 23 of control device 2 receives the sensor signal from A/D converter 19 via I/F 11 and executes the program stored in ROM 24 to obtain the Nth derivative of a pulse waveform based on the sensor signal (S209). The sphygmographic waveform is divided based on the derivative result to extract a pulse waveform of one beat (S211). Then, the sphygmographic waveform is classified (S213). The classification method carried out at step S213 will be described in detail afterwards.

A predetermined characteristic point is extracted from the classified pulse waveform (S215). Then, the AI (Augmentation Index) value is calculated (S217). Thus, the sensor signal analysis process ends.

The aforementioned AI is a well known index, which is an indexed version of the characteristic value reflecting the intensity of pulse wave reflection corresponding to the arteriosclerosis of central blood vessel (a reflecting phenomenon of pulse wave, representing the susceptible blood stream). It is said that AI is an effective index for an early diagnosis of circulatory disorder, and is known to exhibit a behavior different from that of blood pressure.

Figure 4:
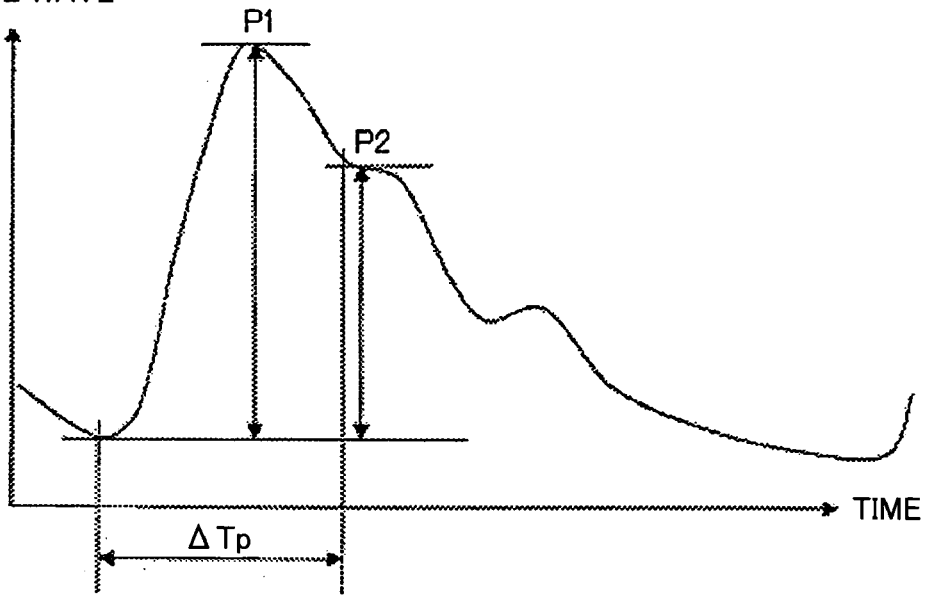
FIGS. 4 and 5 show specific examples of change in the measured pulse wave over time.
Figure 5:
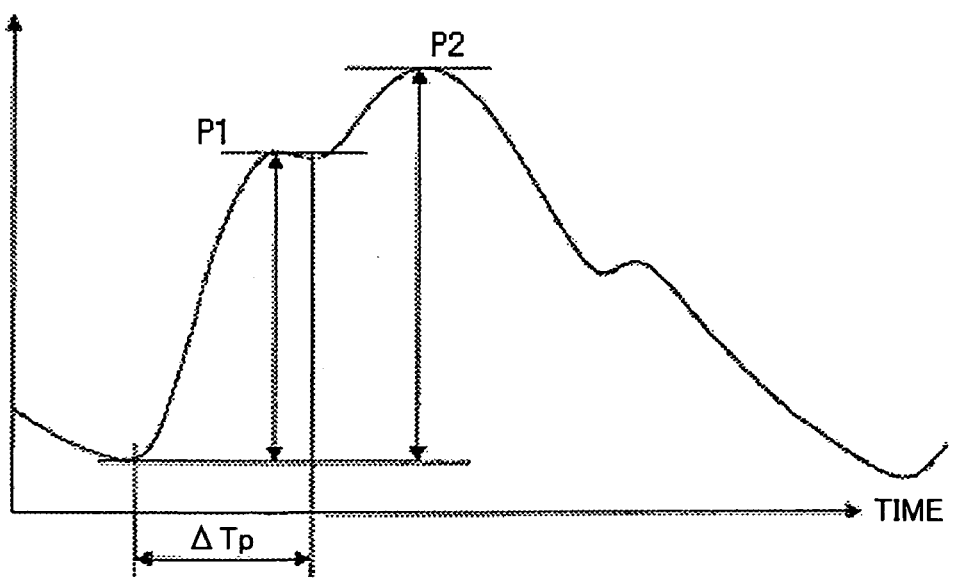

In further detail, description is provided based on the specific examples of FIGS. 4 and 5 showing change in the measured pulse wave over time. For example, the AI value is obtained as AI=P1/P2 (or AI (%)=(P2−P1)/P1×100) when the pulse wave shown in FIG. 4 is measured. The AI value is obtained as AI=P1/P2 (or AI (%)=(P2−P1)/P2×100) when the pulse wave shown in FIG. 5 is measured. Level P1 at time T1 indicates the value by the traveling wave of blood (early systolic component) caused by a heart beat, whereas level P2 at time T2 indicates the value by a reflected wave (late systolic component) for the traveling wave caused by a heart beat. The intensity and appearance time of this reflected wave based on the rising point of the ejection wave change, corresponding to the hardening of the blood vessel. One way of determining P1 and P2 is to apply an arithmetic operation such as differentiation on the pulse waveform. In general, a younger subject exhibits the relationship of level P2<level P1, as shown in FIG. 4, whereas an older subject exhibits the relationship of level P2>level P1, as shown in FIG. 5. This is attributed to the advancement of the hardening of the vascular inner wall (arteriosclerosis) as the age of a subject becomes higher. The ejection wave cannot be absorbed sufficiently at the wall of the blood vessel, so that reflection of a high level will be detected within a short period of time. Thus, the AI value is obtained from the traveling wave and reflected wave caused by a heart beat, and is a characteristic value reflecting the intensity of reflection of a pulse wave corresponding to the arteriosclerosis of central blood vessel.

The present embodiment is described in which the AI value is calculated as the characteristic value of a pulse wave. In the present embodiment, the characteristic value is not limited to an AI value, and a similar advantage can be obtained by using other values such as $\Delta Tp$ shown in FIGS. 4 and 5, for example, as the characteristic values. This $\Delta Tp$ is a well known index likewise AI.

Figure 6:
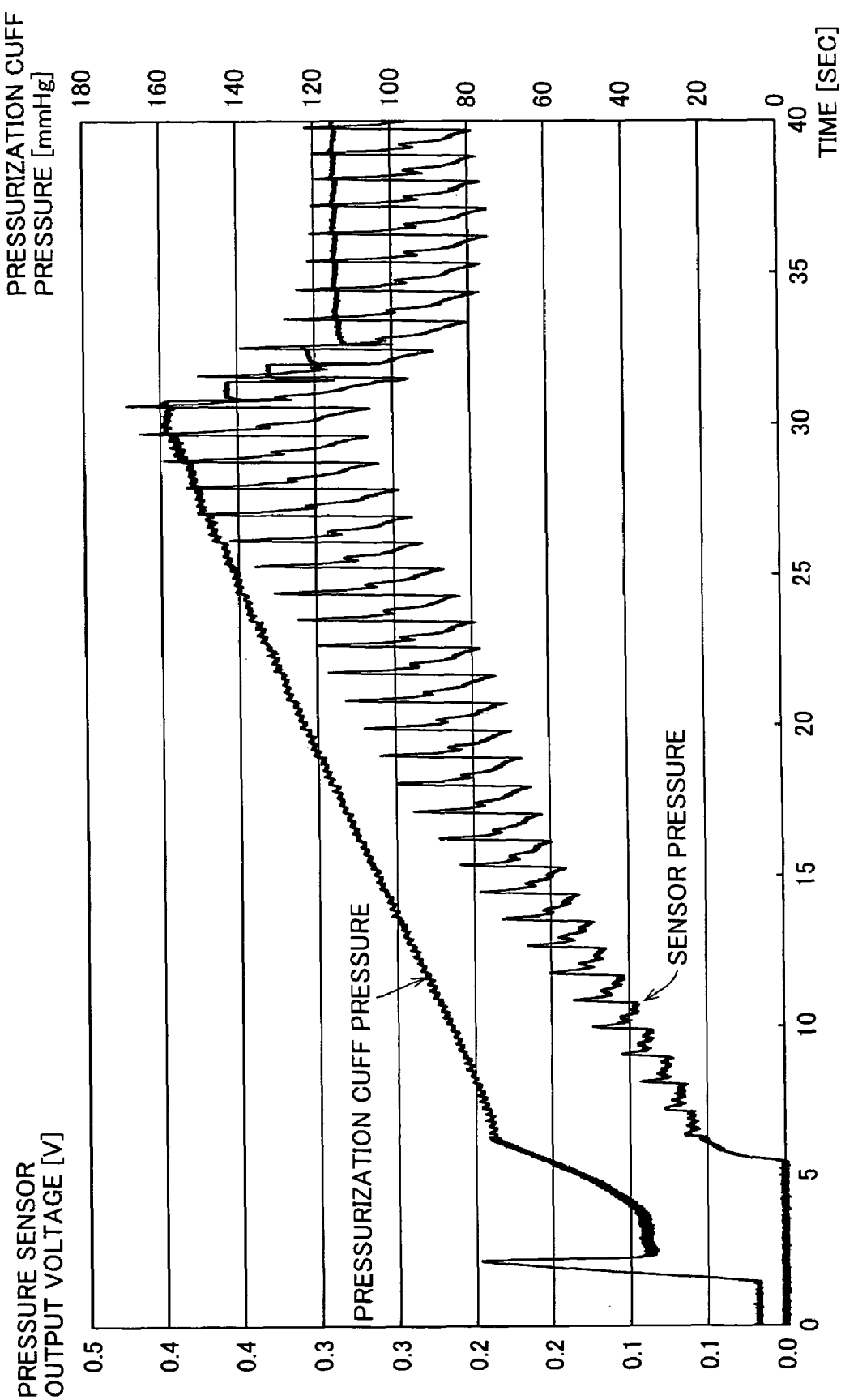
FIG. 6 shows a specific example of the output change of a sensor signal (pulse waveform).

A specific example of change in the sensor signal (pulse waveform) detected by semiconductor pressure sensor 17 is shown in FIG. 6. In FIG. 6, the level of the voltage signal output from semiconductor pressure sensor 17 and the pressurization level of pressurization cuff 16 with respect to the sensor region are plotted along the ordinate, whereas the elapse of the pulse wave measurement time is plotted along the abscissa.

Figure 7:
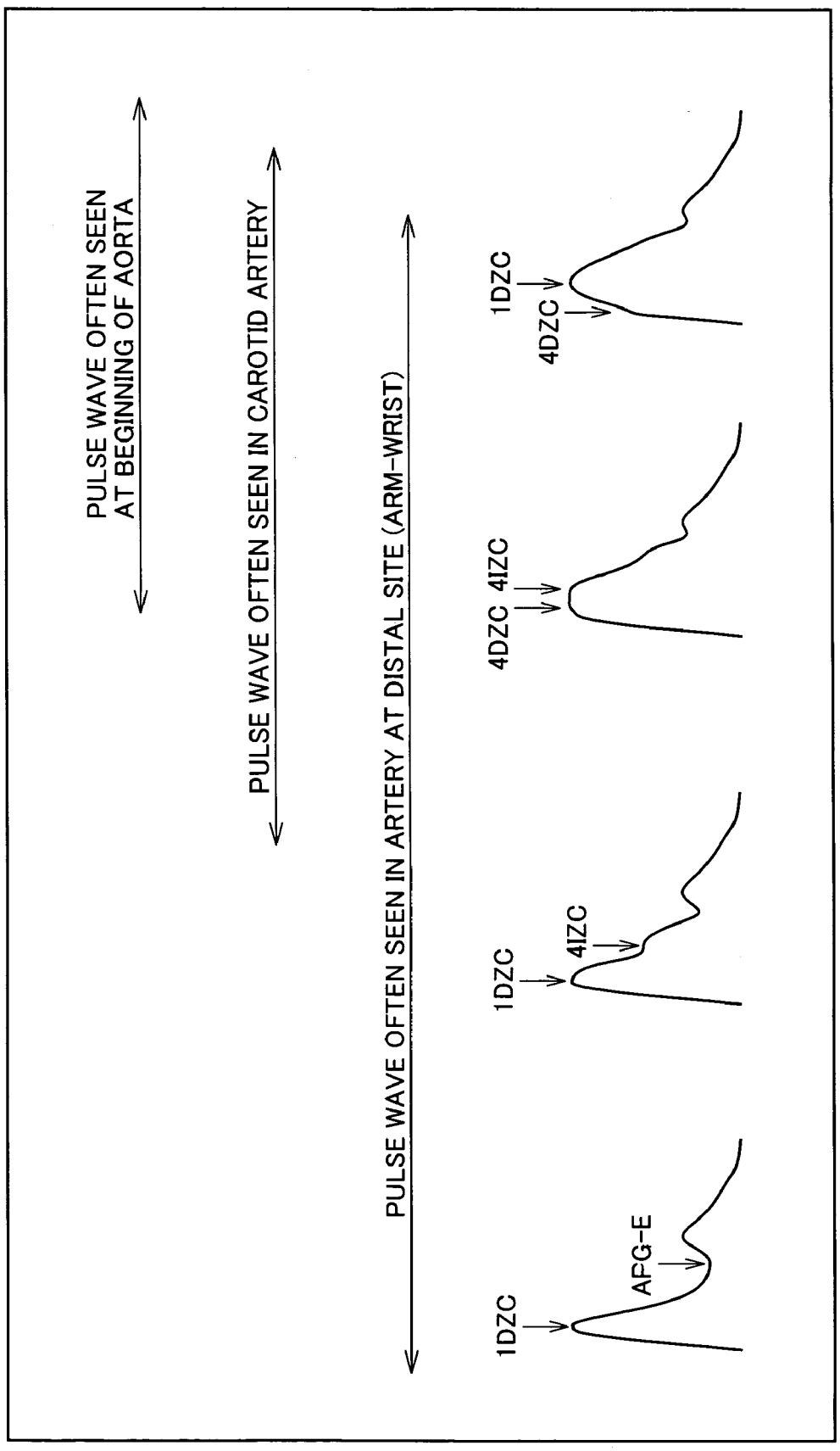
FIG. 7 shows a specific example of characteristic waveform shapes of the pulse waveform.
Figure 8:
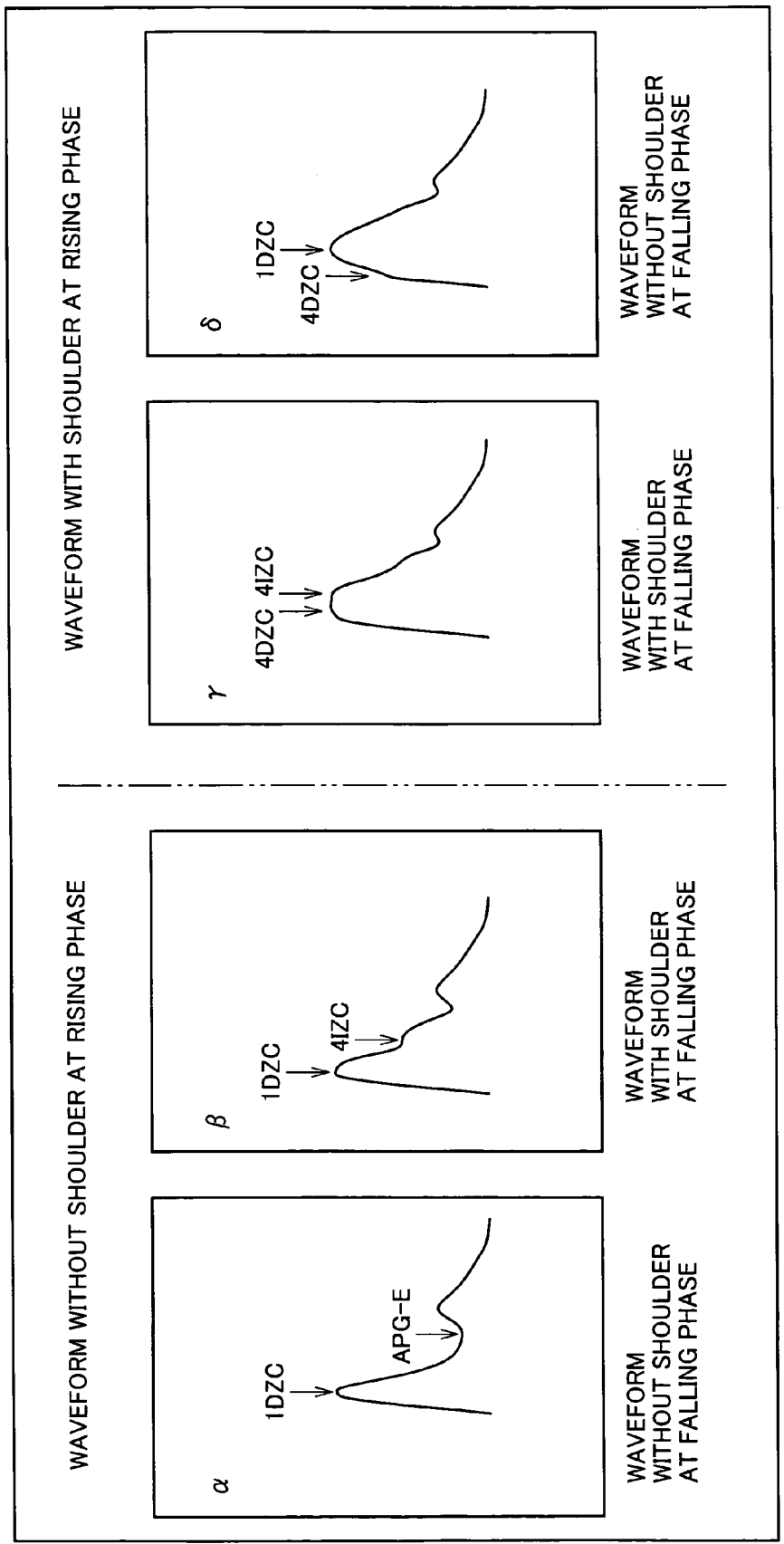
FIG. 8 shows a specific example of pulse waveform classification.

Based on pulse waveforms as shown in FIG. 6, the characteristics of pulse waveforms focusing on the pulse waveform of one beat are as shown in FIG. 7. In other words, a pulse wave is a superposed wave of a traveling wave corresponding to the pressure of blood ejected from the heart and a reflected wave corresponding to the reflected pressure of blood ejected from the heart. The waveform shows different characteristics depending upon the measurement site and subject. More specifically, as shown in FIG. 8, the waveforms are classified into waveforms with and without inflection points called shoulders at the rising phase of pulse waveforms (right side and left side of the center chain dotted line in FIG. 8), and also classified into waveforms with and without shoulders at the falling phase, depending upon the manner of superposition (matching degree) of the traveling wave and reflected wave. In accordance with such classification: any waveform with no shoulder at both the rising phase and falling phase in the pulse waveform is called α waveform; any waveform with no shoulder at the rising phase and with a shoulder at the falling phase of the pulse waveform is called β waveform; any waveform with a shoulder at both the rising phase and falling phase in the pulse waveform is called γ waveform; and any waveform with a shoulder at the rising phase and no shoulder at the falling phase in the pulse waveform is called δ waveform.

Figure 9:
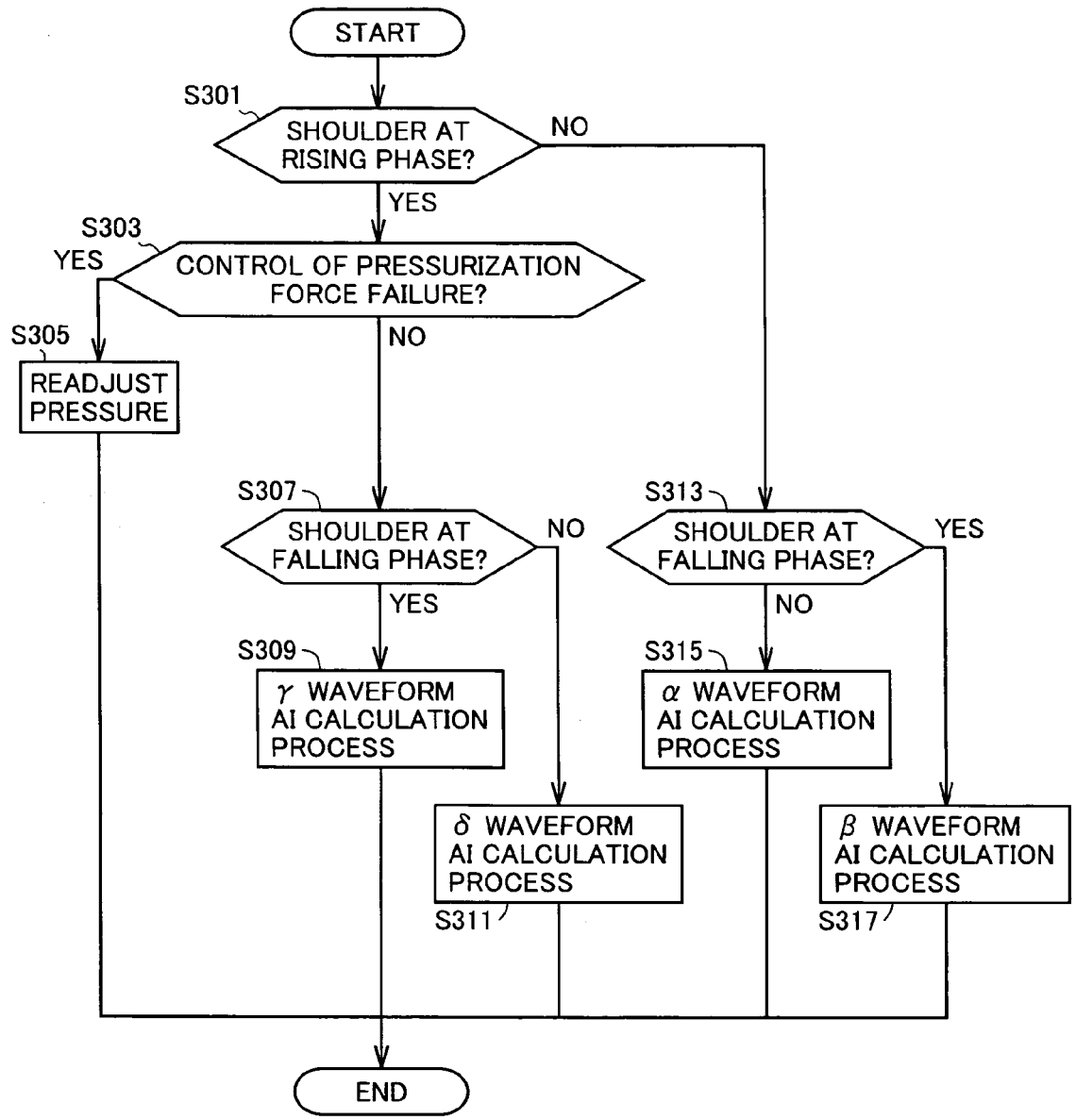
FIG. 9 is a flow chart of a characteristic value calculation process carried out at the pulse wave measuring apparatus of the embodiment.

The pulse wave measuring apparatus of the present invention is characterized in that pulse waveforms obtained by measurement are classified as set forth above to calculate the AI value that is the characteristic value in accordance with the result. In other words, the process shown in the flow chart of FIG. 9 is executed to classify pulse waveforms as set forth above, and the AI value is calculated based on the result. The process in accordance with the flow chart of FIG. 9 corresponds to the process of steps S211-S217 of FIG. 3 set forth before. In a similar manner, the process of FIG. 9 is realized by CPU 23 of control device 2, establishing access to ROM 24 to read out the program therefrom, which is transferred onto RAM 25 for execution.

Referring to FIG. 9, CPU 23 determines the presence/absence of a shoulder at the rising phase in the pulse waveform obtained from pulse wave device 1 via I/F 11 (S301). Further determination is made of the presence/absence of a shoulder at the falling phase (S307, S313). The pulse waveform is classified into waveform α-δ to calculate an AI value according to the AI value calculation process for each different type of waveform (S309, S311, S315, S317). Then, the present process ends.

Further, when there is a shoulder at the rising phase in the pulse waveform at step S301 (YES at S301), and determination is made of control of pressurization of pressurization cuff 16 has failed (YES at S303), CPU 23 readjusts the pressurization force of pressurization cuff 16 (S305), and the present process ends.

In the process of FIG. 9, the presence/absence of a shoulder at the rising phase in the pulse waveform is first made, and then determination of the presence/absence of a shoulder at the falling phase is made. This order of determination is not limited to that described here. The order of determination may be opposite.

Classification of a pulse waveform will be described in further detail hereinafter.

Notation of respective characteristic points in a waveform is defined as follows:

1IDZC: positive-to-negative zero crossing point of first derivative

4DZC: positive-to-negative zero crossing point of fourth derivative

4IZC: negative-to-positive zero crossing point of fourth derivative

APG-A: acceleration pulse wave point A
APG-B: acceleration pulse wave point B
APG-E: acceleration pulse wave point E
APG-F: acceleration pulse wave point F The above 1DZC (positive-to-negative zero crossing point) is a point on a waveform corresponding to point zero at the transition from + to − of first derivative, and represents the maximum such as the pulse wave highest point. 4DZC is a point on a waveform corresponding to point zero at the transition from + to − of fourth derivative, whereas 4IZC (negative-to-positive zero crossing point) is a point on a waveform corresponding to point zero at the transition from − to + of fourth derivative, both representing an inflection point or distortion (shoulder) in a waveform. APG-A to APG-F are points on a waveform corresponding to respective points A-F, where A-F are respective peaks of second derivative, representing the characteristics of respective waveforms.

Figures 10, 11:
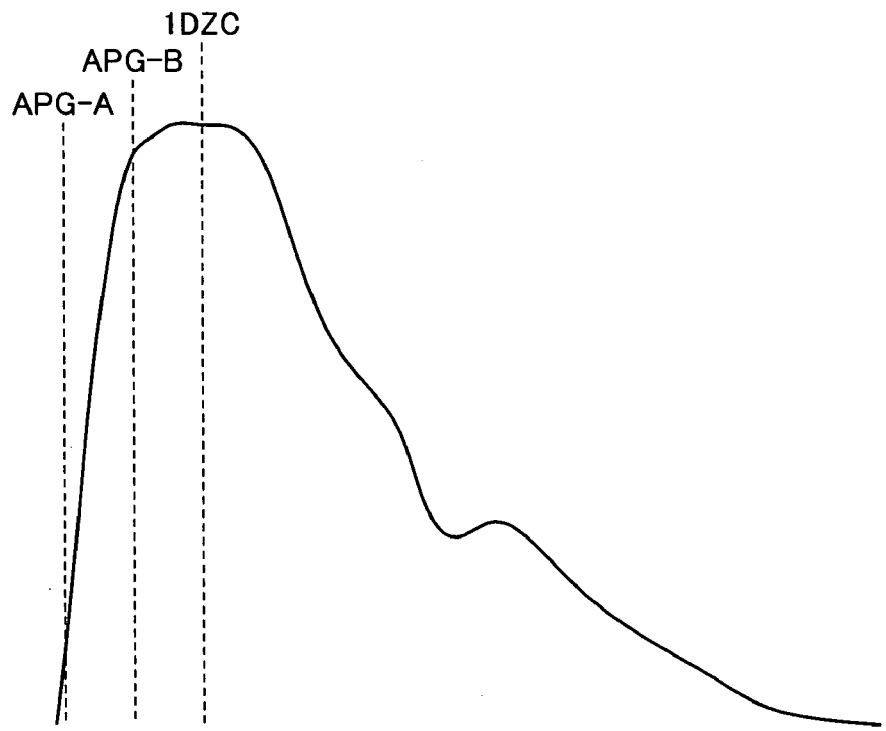
FIG. 10 shows a specific example of major classification of pulse waveforms.
FIG. 11 shows a specific example of a classification table of major-classified pulse waveforms.

Prior to the above-described classification of a pulse waveform, CPU 23 obtains a multi-dimensional derivative of the obtained pulse waveform to calculate each characteristic point. At step S301, CPU 23 classifies on a large scale waveforms into the α, β type, or γ, δ type in accordance with the inflection of each characteristic point, focusing on the number and respective positions of 4DZCs located in the region between APG-A point to 1DCZC point (rising phase), as shown in FIG. 10. The α and β type waveforms are waveforms whose traveling wave is relatively greater than the reflected wave in the superposed wave, whereas the γ and δ type waveforms are waveforms whose reflected wave is greater than the traveling wave in the superposed wave.

A specific example of a classification table of pulse waveforms for major classification based on the number and positions of 4DZCs is shown in FIG. 11. Referring to FIG. 11, when there are three or more 4DZC points in the region of APG-A point-APG-B point and the region of APG-B point-1DZC point, determination is made of an error based on the type classification since there are too many waveform distortions. The possibility of excessive pressurization of pressurization cuff 16 is high. In other words, CPU 23 determines in such a case that the control of pressurization of pressurization cuff 16 has failed at step S303 (YES at S303). Then, CPU 23 proceeds to step S305 to carry out readjustment so as to reduce the pressurization force of pressurization cuff 16.

In the case where there is one 4DZC point in the region of APG-A point-APG-B point and zero to one 4DZC point in the region of APG-B point-1DZC point, or when there is no 4DZC point in the region of APG-A point-APG-B point and one 4DZC point in the region of APG-B point-1DZC-point, CPU 23 determines that the pulse waveform is the γ waveform type or δ waveform type. When there is no 4DZC point in the region of APG-A point-APG-B point and in the region of APG-B point-1DZC point, CPU 23 determines that the pulse waveform is the α waveform type or β waveform type.

Figure 12:
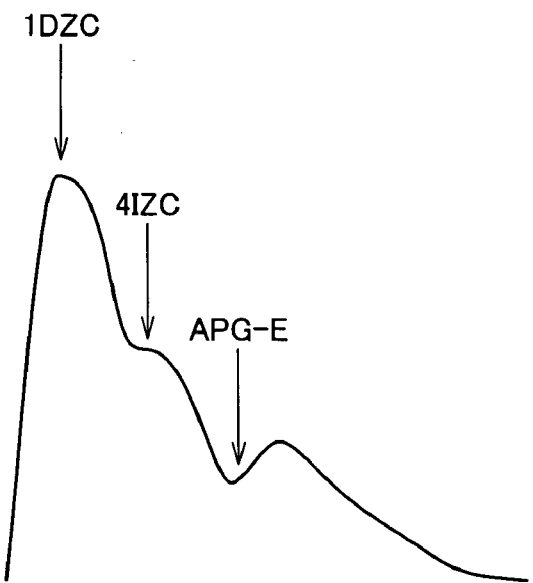
FIGS. 12 and 13 show specific examples of sub-classification of pulse waveforms.

At step S313, CPU 23 further classifies the waveform into the α waveform type or β waveform type, based on the presence/absence of 4IZC (shoulder) at the region of 1IDZC point-APG-E point (falling phase), as shown in FIG. 12. This sub-classification is described in detail here. At step S313, CPU 23 scans the fourth derivative from the 1IDZC point, and determines that the pulse waveform is the β waveform type if there is a negative-to-positive zero crossing point (4IZC) in the region where the third derivative is negative in the region up to APG-E point. When there are a plurality of 4IZC points, the 4IZC point with the smallest third derivative is employed. If there is no negative-to-positive zero crossing point (4IZC) in the region of 1DZC point-APG-E point, the pulse waveform is determined as the α waveform type.

Figure 13:
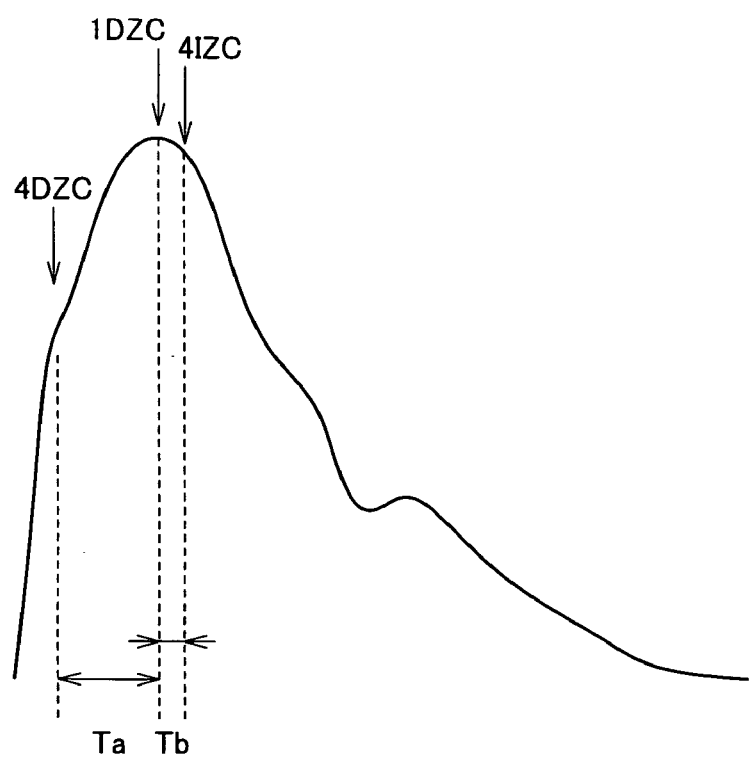
Figure 15:
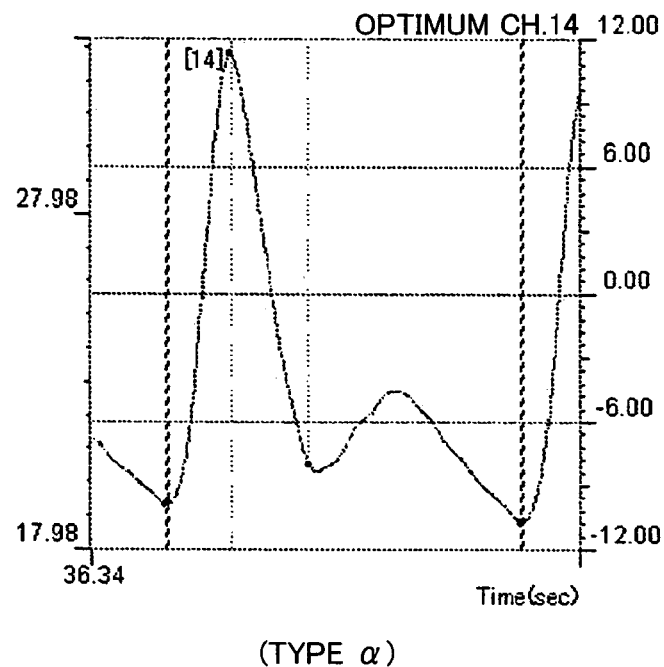
FIGS. 15, 16, 17 and 18 show output examples of α, β, γ and δ waveforms, respectively.
Figure 16:
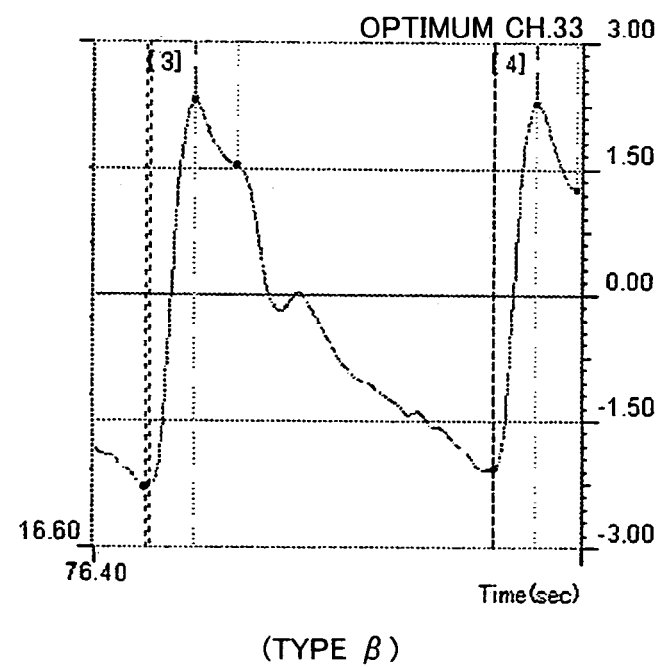
Figure 17:
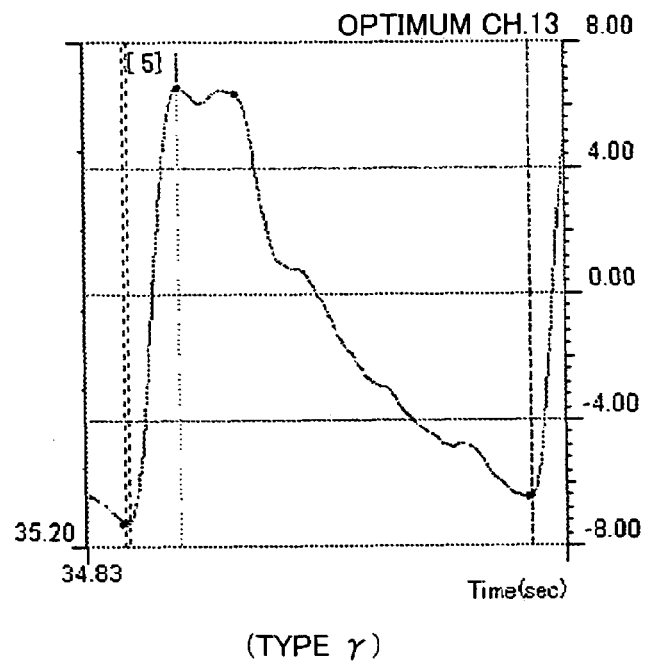
Figure 18:
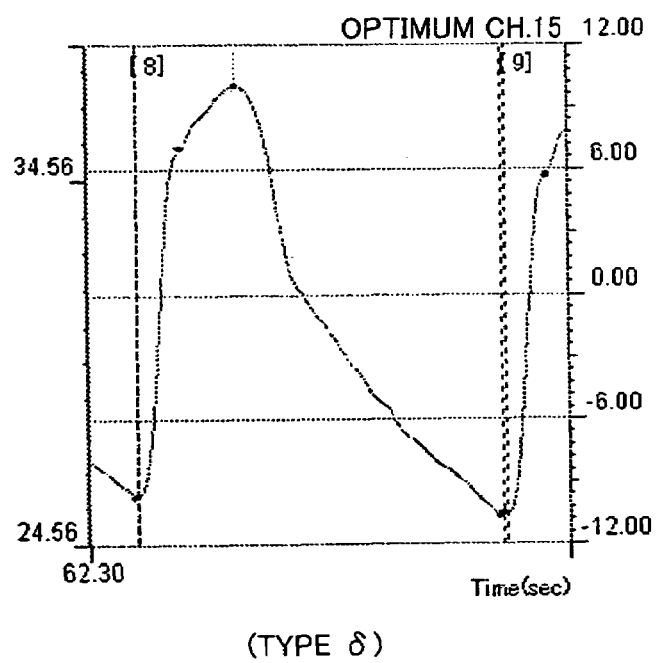

Additionally, at step S307, CPU 23 calculates time Ta of 4DZC point-1DZC point and time Tb of 1DZC point-4IZC point shown in FIG. 13, and further classifies the waveforms into the γ waveform type or δ waveform type based on the relation of the calculated time. Specifically, at step S307, CPU 23 determines that the pulse waveform is the γ waveform type when Ta≦Tb×1 is satisfied. CPU 23 determines that the pulse waveform is the δ waveform type when the relationship of Ta≦Tb×1 is not satisfied.

FIG. 14 shows a scheme of the classification of pulse waveforms determined as set forth above. FIG. 14 also shows the characteristic point used in obtaining the AI value for each waveform. The present pulse wave measuring apparatus calculates the AI value using the amplitude of the characteristic point shown in FIG. 14 as the characteristic point representing the traveling wave and reflected wave for each classified waveform.

The calculation method of the AI value for each waveform will be described hereinafter.

$P_{PEAK}$: Peak point pressure (highest pressure during one beat)
$P_{SYS1}$: First systolic pressure (pressure of traveling wave)
$P_{SYS2}$: Second systolic pressure (pressure of reflected wave)
$P_{DIA}$: Diastolic pressure (lowest pressure during one beat)
SBP: Systolic blood pressure
DBP: Diastolic blood pressure Based on the above definition, CPU 23 calculates the AI value using the following equation (1) at step S315 when the pulse waveform is the α waveform type.

$$AI = \frac{P_{APG-E} - P_{DIA}}{P_{Peak} - P_{DIA}} \quad (1)$$

$$P_{DIA} = DBP$$

$$P_{SYS1} = P_{PEAK} = SBP$$

$$P_{SYS2} = P_{APG-E}$$

When the pulse waveform is the β waveform type, CPU 23 calculates the AI value using the following equation (2) at step S317.

$$AI = \frac{P_{4IZC} - P_{DIA}}{P_{Peak} - P_{DIA}} \quad (2)$$

$$P_{DIA} = DBP$$

$$P_{SYS1} = P_{PEAK} = SBP$$

$$P_{SYS2} = P_{4IZC}$$

When the pulse waveform is the γ waveform type, CPU 23 calculates the AI value based on the following equation (3) at step S309.

$$AI = \frac{P_{4IZC} - P_{DIA}}{P_{4DZC} - P_{DIA}} \quad (3)$$

$$P_{DIA} = DBP$$

$$P_{SYS1} = P_{4DZC}$$

$$P_{SYS2} = P_{4IZC}$$

$$P_{PEAK} = SBP$$

When the pulse waveform is the δ waveform type, CPU 23 calculates the AI value using the following equation (4) at step S311.

$$AI = \frac{P_{Peak} - P_{DIA}}{P_{ADZC} - P_{DIA}} \quad (4)$$

$$P_{DIA} = DBP$$

$$P_{SYS1} = P_{4DZC}$$

$$P_{SYS2} = P_{PEAK} = SBP$$

Specific output examples of waveform types α-δ identified in pulse waveforms actually measured are shown in FIGS. 15-18.

Figure 19:
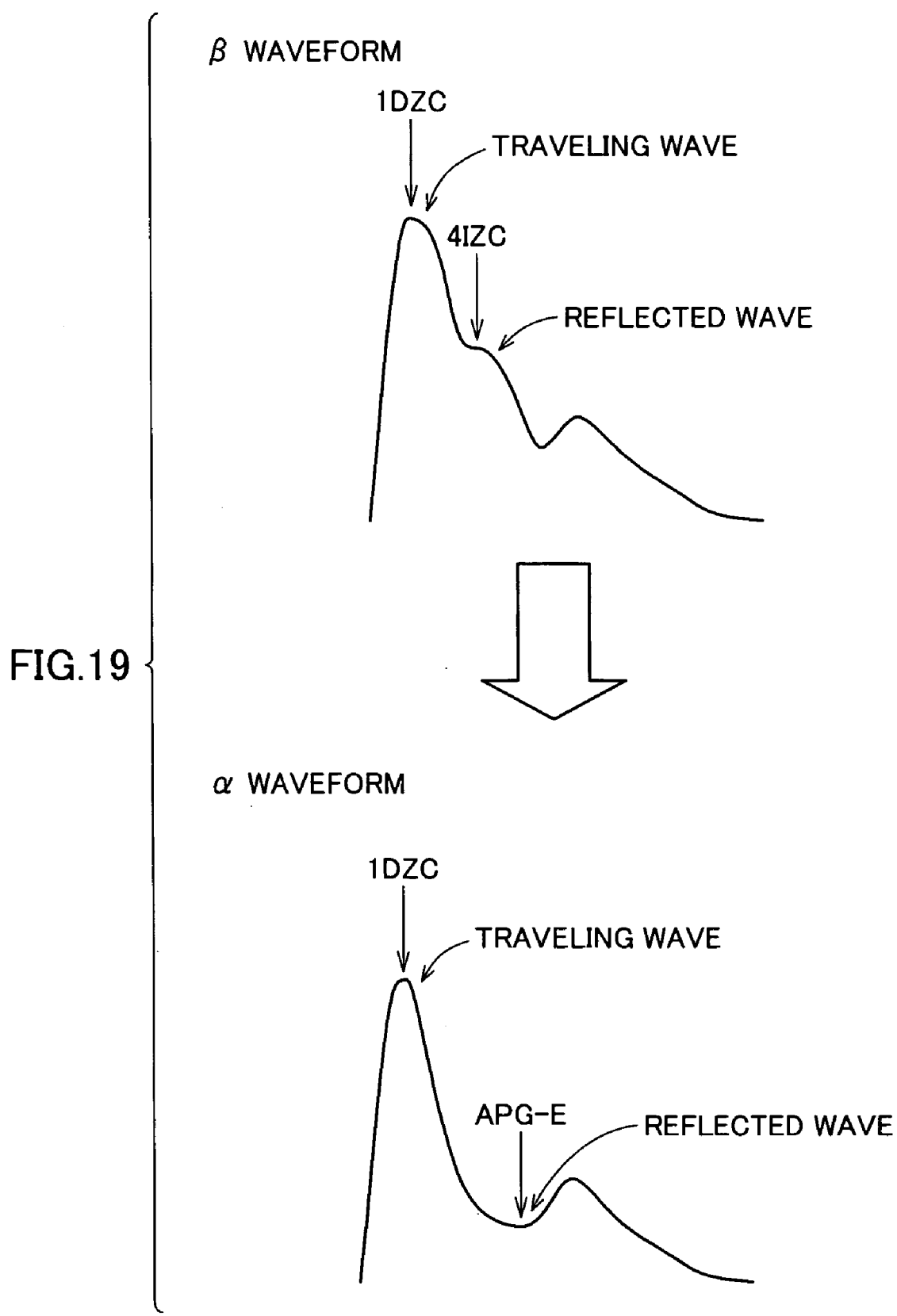
FIG. 19 shows change from β waveform to α waveform.
Figure 20:
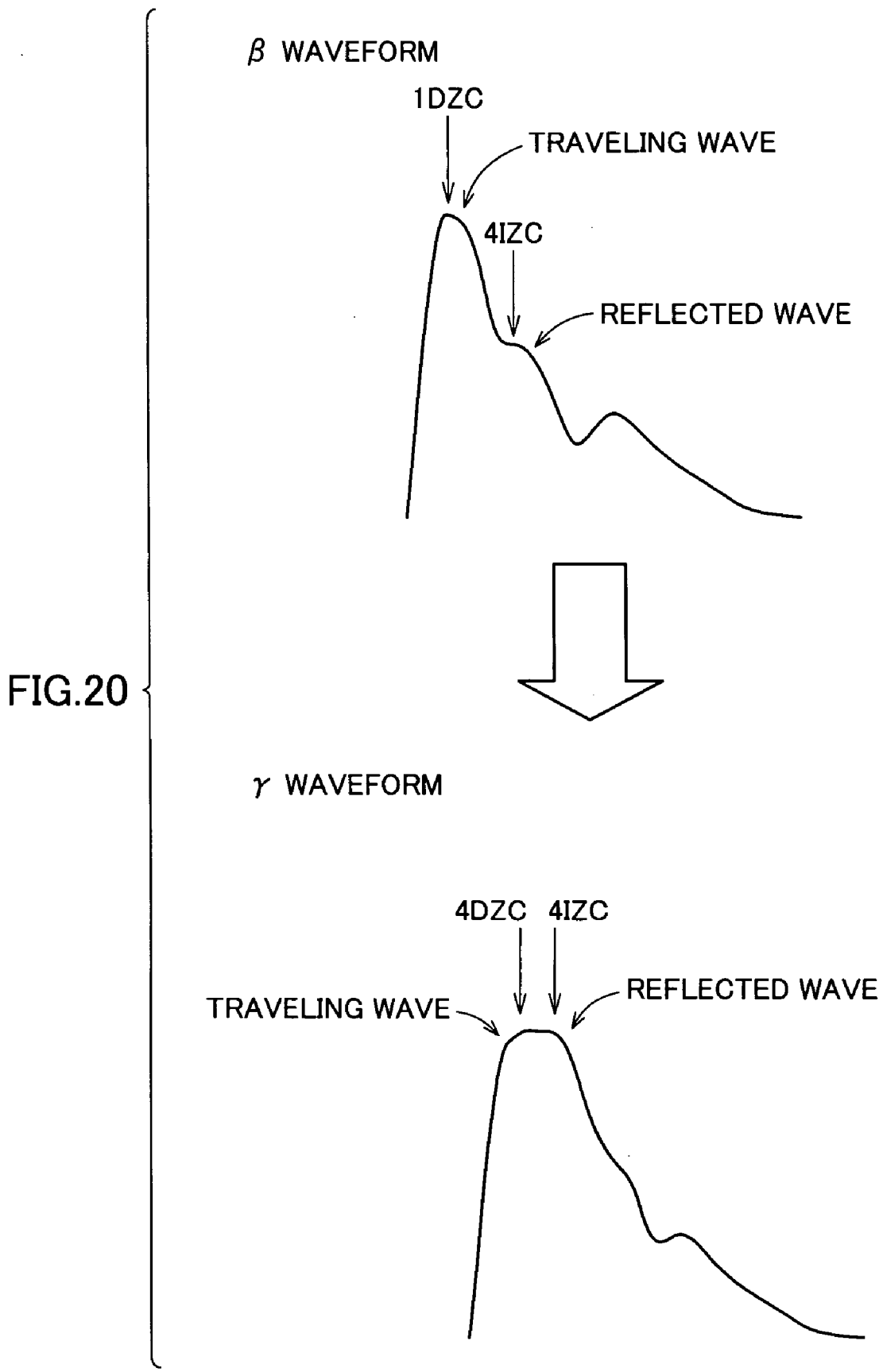
FIG. 20 shows change from β waveform to γ waveform.
Figure 21:
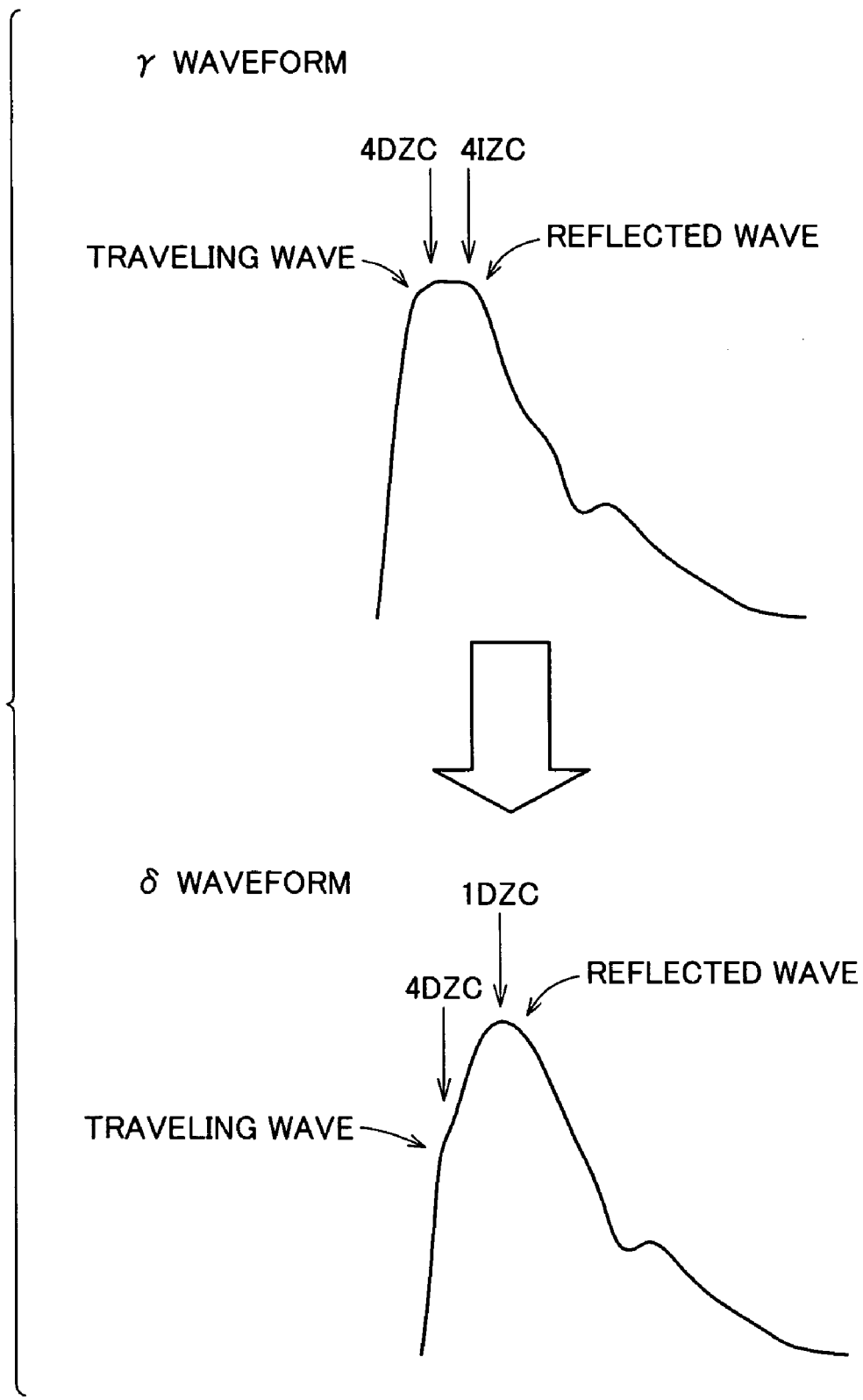
FIG. 21 shows change from γ waveform to δ waveform.

As previously mentioned, the pulse waveform changes depending upon the measurement site. As specifically shown in FIG. 19, in the case where the measurement site changes from the central area to the distal area, the β waveform has the 4IZC point (negative-to-positive zero crossing point of fourth derivative) lowered in accordance with the reduction of the reflected wave. Eventually, the 4IZC point matches the APG-E point. Thus, the β waveform is gradually turned into the α waveform. FIG. 20 corresponds to the opposite case where the measurement site changes from the distal area to the central area. The β waveform has the 4IZC point raised in accordance with the increase of the reflected wave. Accordingly, the 1DZC point gradually becomes the peak of the superposed wave. Thus, the β waveform is smoothly turned into the γ waveform. FIG. 21 also corresponds to a case where the measurement site changes from the distal area to the central area. The γ waveform has the 4IZC point raised in accordance with the increase of the reflected wave. The 4IZC point gradually matches the 1DZC point. Thus, the γ waveform smoothly turns into the δ waveform. In other words, the classified waveforms α-δ of the pulse waveform change continuously. The classification of the pulse waveform may vary even if the pulse wave is measured continuously. The above-described continuous change in the classification of the pulse waveform occurs depending upon the generated timing or level of the reflected wave in accordance with the hardness of the vascular wall even if the pulse wave is measured at the same site.

However, the pulse wave measuring apparatus of the present embodiment can accommodate such continuous change in the classification of pulse waveforms since the classification of the pulse waveform is switched to either the α/β waveform or γ/δ waveform in accordance with the presence/absence of the 4DZC point (positive-to-negative zero crossing point of fourth derivative) in the region from the pulse wave lowest point to the pulse wave highest point of the pulse waveform of one beat at step S301 to carry out the subsequent process. In other words, the pulse wave measuring apparatus of the present embodiment switches the position of the traveling wave in the pulse waveform of one beat in accordance with the presence/absence of the 4DZC point (positive-to-negative zero crossing point of fourth derivative) between the pulse wave lowest point to the pulse wave highest point (rising phase) in the pulse waveform of one beat at step S301 to carry out the subsequent process. More specifically, the position of the traveling wave is switched to the position of the pulse wave highest point (1DZC point) when there is no 4DZC point between the pulse wave lowest point and pulse wave highest point (rising phase) of the pulse waveform of one beat, and to the position of the 4DZC point, when present, between the pulse wave lowest point and pulse wave highest point (rising phase) of the pulse waveform of one beat.

In the case where the pulse waveform changes continuously from the γ waveform to the β waveform, the 4DZC point gradually approximates the pulse wave highest point (1DZC point). At the complete transition to the β waveform, the 4DZC point matches the pulse wave highest point and is indiscernible. Therefore, the characteristic value identifying the traveling wave is correspondingly switched by the transition from the γ waveform to the β waveform. The position of the characteristic value will exhibit a continuous change in position. Thus, the AI value calculated at step S309 upon classification of a certain waveform as the γ waveform will approximate the AI value calculated at step S317 based on classification of a waveform which is a continuously transformed waveform version of the certain waveform as the β waveform.

Similarly, the pulse wave measuring apparatus of the present embodiment can accommodate continuous change in the classification of the pulse waveform since the classification of the pulse waveform is switched to either the α or β waveform or the γ or δ waveform in accordance with the presence/absence of the 4IZC point (negative-to-positive zero crossing point of fourth derivative) between the pulse wave highest point and notch point (APG-E point) (falling phase) of the pulse waveform of one beat at step S307 or step S313 to carry out the subsequent process. In other words, the pulse wave measuring apparatus of the present embodiment switches the position of the reflected wave in the pulse waveform of one beat in accordance with the presence/absence of the 4IZC point (negative-to-positive zero crossing point of fourth derivative) between the pulse wave highest point and notch point (falling phase) of the pulse waveform of one beat at step S307 or step S313 to carry out the subsequent process. The position of the reflected wave is switched to the position of the acceleration pulse wave point E (APG-E point) or pulse wave highest point (1DZC point) when there is no 4IZC point between the pulse wave highest point and notch point (falling phase) in the pulse waveform of one beat, and to the position of the 4IZC point, when present, between the pulse wave lowest point and pulse wave highest point (rising phase) in the pulse waveform of one beat.

In the case where the pulse waveform changes continuously from the γ waveform to the δ waveform, the 4IZC point gradually approximates the pulse wave highest point (1DZC point). At the complete transition to the δ waveform, the 4IZC point matches the pulse wave highest point and is indiscernible. Therefore, the characteristic value identifying the traveling wave is correspondingly switched by the transition from the γ waveform to the δ waveform. The position of the characteristic value will exhibit a continuous change in position. Thus, the AI value calculated at step S309 upon classification of a certain waveform as the γ waveform will approximate the AI value calculated at step S311 based on classification of a waveform which is a continuously transformed waveform version of the certain waveform as the δ waveform.

In the case where the pulse waveform changes continuously from the β waveform to the α waveform, the 4IZC point gradually approximates the notch point (APG-E point)). At the complete transition to the α waveform, the 4IZC point matches the notch point and is indiscernible. Therefore, the characteristic value identifying the traveling wave is correspondingly switched by the transition from the β waveform to the α waveform. The position of the characteristic value will exhibit a continuous change in position. Thus, the AI value calculated at step S317 upon classification of a certain waveform as the β waveform will approximate the AI value calculated at step S315 based on classification of a waveform which is a continuously transformed waveform version of the certain waveform as the α waveform.

As described above, the present pulse wave measuring apparatus is characterized in that the input pulse waveform is classified based on the presence of the characteristic point of multi-dimensional derivative (characteristic point of fourth derivative), and a processing method (AI value calculation method) is selected based on the classification result. The present pulse wave measuring apparatus is characterized in that, in the selected processing method, a characteristic point used in another processing method and that can approximate the first characteristic point required in the selected processing method can be used instead of the first characteristic point. This means that the pulse wave measuring apparatus of the present invention can calculate a traveling wave and reflected wave from a pulse wave that is a superposed wave even if a certain characteristic point of multi-dimensional derivative is absent. Furthermore, the traveling wave and the reflected wave can be calculated automatically from the pulse wave that is a superposed wave even with respect to a different pulse waveform obtained from a different measurement site by executing the same process. Additionally, the characteristic value such as an AI value can be calculated reliably even in the case where the classification of the pulse waveform measured continuously varies.

The present embodiment was described based on using characteristic points of the third or fourth derivative of the pulse waveform as characteristic points. The present invention is not limited to such third or fourth derivatives. Any N-th derivative can be employed as long as it is a multi-dimensional derivative indicating the characteristic of the pulse waveform.

The above description is based on a structure of detecting a pulse wave by tracing change in the pulse pressure using a pressure sensor. The method of detecting a pulse wave is not limited to that described above. A structure of detecting a pulse wave by tracing volumetric change, for example, may be used.

The pulse waveform analysis method of the present invention is not limited to the analysis of a pulse waveform. The present invention can be applied to the analysis of another biological wave corresponding to the superposition of first and second waveforms generated by the contraction and expansion of the heart such as the heart beat waveform. The pulse wave analysis method carried out by the present pulse wave measuring apparatus can be provided as a program. Such a program can be stored in a computer-readable recording medium such as a flexible disc, CD-ROM (Compact Disc-ROM), ROM, RAM, or memory card associated with a computer to be provided as a program product. Alternatively, the program can be stored in a recording medium such as a hard disk incorporated in a computer to be provided as a program. Furthermore, the program can be provided by downloading through a network.

The presented program is installed in a program storage unit such as a hard disk for execution. The program product includes the program itself, and the recording medium in which the program is recorded.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A pulse wave measuring apparatus comprising
a first calculation unit calculating a wave of multi-dimensional derivative from a pulse wave of one beat to obtain a characteristic point of multi-dimensional derivative and
a second calculation unit calculating, based on presence of a certain characteristic point of multi-dimensional derivative calculated by said first calculation unit in a predetermined interval of said pulse wave of one beat, one of an early systolic component and late systolic component corresponding to said predetermined interval, using said certain characteristic point of multi-dimensional derivative,
wherein
said predetermined interval is an interval of a rising phase from a start of said pulse wave of one beat to a pulse wave highest point, and
said second calculation unit calculates the early systolic component using said characteristic point of multi-dimensional derivative when said certain characteristic point of multi-dimensional derivative is present in said rising phase interval.

2. The pulse wave measuring apparatus according to claim 1, wherein said second calculation unit uses said pulse wave highest point in the calculation of said early systolic component when a position of said certain characteristic point of multi-dimensional derivative approximates said pulse wave highest point and said pulse wave is a pulse wave immediately preceding an eventual match of said position of said certain characteristic point of multi-dimensional derivative to said pulse wave highest point to be indiscernible.

3. The pulse wave measuring apparatus according to claim 1, wherein
said predetermined interval is an interval of a falling phase from a pulse wave highest point to a next notch point of said pulse wave highest point, and
said second calculation unit calculates the late systolic component using said characteristic point of a multi-dimensional derivative when said certain characteristic point of multi-dimensional derivative is present in said falling phase interval.

4. The pulse wave measuring apparatus according to claim 3, wherein said second calculation unit uses said pulse wave highest point in the calculation of said late systolic component when a position of said certain characteristic point of multi-dimensional derivative approximates said pulse wave highest point and said pulse wave is a pulse wave immediately preceding an eventual match of said position of said certain characteristic point of multi-dimensional derivative to said pulse wave highest point to be indiscernible.

5. The pulse wave measuring apparatus according to claim 3, wherein said second calculation unit uses said notch point in the calculation of said late systolic component when a position of said certain characteristic point of multi-dimensional derivative approximates said notch point and said pulse wave is a pulse wave immediately preceding an eventual match of said position of said certain characteristic point of multi-dimensional derivative to said notch point to be indiscernible.

6. A pulse wave measuring apparatus comprising:
a first calculation unit calculating a wave of multi-dimensional derivative from a pulse wave of one beat to obtain a characteristic point of multi-dimensional derivative and
a second calculation unit calculating, based on presence of a certain characteristic point of multi-dimensional derivative calculated by said first calculation unit in a predetermined interval of said pulse wave of one beat, one of an early systolic component and late systolic component corresponding to said predetermined interval, using said certain characteristic point of multi-dimensional derivative,
wherein said certain characteristic point of multi-dimensional derivative is a minimum of a wave of third derivative.

7. The pulse wave measuring apparatus according to claim 1, wherein said certain characteristic point of multi-dimensional derivative is a maximum of a wave of third derivative.

8. A biological wave analysis program product causing a computer to execute analysis of a biological wave that is a superposition of a first waveform and second waveform, causing the computer to execute:
a first calculation step of calculating a wave of multi-dimensional derivative from said biological wave of one beat to obtain a characteristic point of multi-dimensional derivative and
a second calculation step of calculating, based on presence of a certain characteristic point of multi-dimensional derivative calculated by said first step of calculating in a predetermined interval of said biological wave of one beat, one of said first waveform and second waveform corresponding to said predetermined interval, using said certain characteristic point of multi-dimensional derivative,
wherein
said predetermined interval is an interval of a rising phase from a start to a highest point of said biological wave of one beat, and
said second calculation step calculates said first waveform using said characteristic point of multi-dimensional derivative when said certain characteristic point of multi-dimensional derivative is present at said rising phase interval.

9. The biological wave analysis program product according to claim 8, wherein said second calculation step uses said highest point in the calculation of said first waveform when a position of said certain characteristic point of multi-dimensional derivative approximates said highest point and said biological wave is a biological wave immediately preceding an eventual match of said position of said certain characteristic point of multi-dimensional derivative to said highest point to be indiscernible.

10. The biological wave analysis program product according to claim 8, wherein said predetermined interval is an interval of a falling phase from the highest point to a next notch point of said highest point, and said second calculation step calculates said second waveform using said characteristic point of multi-dimensional derivative when said certain characteristic point of multi-dimensional derivative is present in said falling phase interval.

11. The biological wave analysis program product according to claim 10, wherein said second calculation step uses said highest point in the calculation of said second waveform when a position of said certain characteristic point of multi-dimensional derivative approximates said highest point and said biological wave is a biological wave immediately preceding an eventual match of said position of said certain characteristic point of multi-dimensional derivative to said highest point to be indiscernible.

12. The biological wave analysis program product according to claim 10, wherein said second calculation step uses said notch point in the calculation of said second waveform when a position of said certain characteristic point of multi-dimensional derivative approximates said notch point and said biological wave is a biological wave immediately preceding an eventual match of said position of said certain characteristic point of multi-dimensional derivative to said notch point to be indiscernible.

13. A biological wave analysis program product causing a computer to execute analysis of a biological wave that is a superposition of a first waveform and second waveform, causing the computer to execute:
a first calculation step of calculating a wave of multi-dimensional derivative from said biological wave of one beat to obtain a characteristic point of multi-dimensional derivative, and
a second calculation step of calculating, based on presence of a certain characteristic point of multi-dimensional derivative calculated by said first step of calculating in a predetermined interval of said biological wave of one beat, one of said first waveform and second waveform corresponding to said predetermined interval, using said certain characteristic point of multi-dimensional derivative,
wherein said certain characteristic point of multi-dimensional derivative is a minimum of a wave of third derivative.

14. The biological wave analysis program product according to claim 8, wherein said certain characteristic point of multi-dimensional derivative is a maximum of a wave of third derivative.

15. A pulse wave measuring apparatus comprising:
a first calculation unit calculating a wave of multi-dimensional derivative from a pulse wave of one beat to obtain a characteristic point of multi-dimensional derivative, and
a second calculation unit calculating, when a certain characteristic point of multi-dimensional derivative calculated by said first calculation unit is present in both a first interval identified as an interval of a rising phase from a start of said pulse wave of one beat to a pulse wave highest point and a second interval identified as an interval of a falling phase from a pulse wave highest point to a next notch point of said pulse wave highest point, an early systolic component using said characteristic point of multi-dimensional derivative present in said first interval and a late systolic component using said characteristic point of multi-dimensional derivative present in said second interval.

16. A computer-readable medium containing instructions for causing a computer to execute analysis of a pulse wave, causing the computer to execute:

a first calculation step of a calculating a wave of multi-dimensional derivative from a pulse wave of one beat to obtain a characteristic point of multi-dimensional derivative, and a second calculation step of calculating, when a certain characteristic point of multi-dimensional derivative calculated by said first calculation step is present in both a first interval identified as an interval of a rising phase from a start of said pulse wave of one beat to a pulse wave highest point and a second interval identified as an interval of a falling phase from a pulse wave highest point to a next notch point of said pulse wave highest point, an early systolic component using said characteristic point of multi-dimensional derivative present in said first interval and a late systolic component using said characteristic point of multi-dimensional derivative present in said second interval.

* * * * *